United States Patent [19]

Swonger et al.

[11] 4,015,240
[45] Mar. 29, 1977

[54] PATTERN RECOGNITION APPARATUS

[75] Inventors: Claron W. Swonger, Elma; Hollis F. Ryan, Cheektowaga, both of N.Y.; Robert M. Stock, Severna Park, Md.; Charles M. Vossler, Williamsville, N.Y.

[73] Assignee: Calspan Corporation, Buffalo, N.Y.

[22] Filed: Feb. 12, 1975

[21] Appl. No.: 549,399

Related U.S. Application Data

[63] Continuation of Ser. No. 349,349, April 9, 1973, abandoned.

[52] U.S. Cl. .................................. 340/146.3 E
[51] Int. Cl.² .................................. G06K 9/12
[58] Field of Search .......... 340/146.3 E, 146.3 MH, 340/146.3 H, 146.3 AG, 146.3 AC

[56] References Cited
UNITED STATES PATENTS

| | | | |
|---|---|---|---|
| 3,196,398 | 7/1965 | Baskin | 340/146.3 H |
| 3,582,889 | 6/1971 | Bodez | 340/146.3 E |
| 3,613,080 | 10/1971 | Angeloni et al. | 340/146.3 MA |
| 3,723,970 | 3/1973 | Stoller | 340/146.3 H |
| 3,737,855 | 6/1973 | Cutaia | 340/146.3 AG |
| 3,761,876 | 9/1973 | Flaherty et al. | 340/146.3 AG |

*Primary Examiner*—Leo H. Boudreau
*Attorney, Agent, or Firm*—Allen J. Jaffe

[57] ABSTRACT

A pattern recognition apparatus for recognizing or identifying fingerprint images and the like is described. The apparatus enables the determination of the coordinates and angular positions of characteritic points such as fingerprint minutiae. The pattern recognition apparatus includes a high resolution scanner for scanning a fingerprint impression or image, an analog to digital converter to convert the scanner signals to a digitally encoded image having many levels of gray scale data, an image enhancer to eliminate imperfections in the imagery, pre-editing circuits to edit out areas of the image which should not be further processed, a minutiae detection system having high redundancy to reduce the probability of missed minutiae, and a post-editing subsystem to eliminate false minutiae detections.

7 Claims, 4 Drawing Figures

PATTERN RECOGNITION APPARATUS

This is a continuation of application Ser. No. 349,349, filed Apr. 9, 1973 and now abandoned.

The present invention relates to pattern recognition apparatus and, more particularly, to such apparatus which is utilized for the automatic recognition and identification of fingerprint and/or other similar patterns.

There are previously known systems for automatically identifying fingerprint images which have as their objective the location of certain points in the image that are uniquely characteristic of an individual's fingerprint. These points are termed minutiae and consist of line or ridge endings or bifurcations existing in the total contour pattern of the fingerprint.

Any system of this general type to be suited for actual field use must be capable of accomplishing certain critical requirements and objectives, foremost among which is the requirement for accuracy in identifying the characteristic points despite the variations introduced in the process of obtaining the fingerprint impression or image. On a wide variety of fingerprint card backgrounds, prints are rolled on a card which may contain printing and other classifying marks. The inked fingerprint impression is characterized by wide variations in the inking of the finger, variations in pressure during rolling of the print and twisting or other smearing actions which tend to degrade the quality of the fingerprint impression. Temporary degradation of the original fingerprint such as that caused by cuts, warts, partial scraping away of ridges, scars, callouses must also be taken into account; otherwise a large proportion of false minutiae would be indicated. Examination of an average quality fingerprint quickly reveals that if every "apparent" ridge ending (including false ones) on the print was treated as an actual ridge ending, the true minutiae would be completely lost among the far more prevalent false minutiae on the fingerprint.

Another critical requirement for acceptance by law enforcement agencies of an automatic fingerprint reader or recognizer relates to the machine's capacity to rapidly and accurately process the data. A single fingerprint includes approximately one-quarter million usable, resolvable points, each having approximately 16 levels (4 bits) of gray scale information. This means that approximately one million bits that constitute the fingerprint impression or image must be analyzed and converted to the 100 points which typically represent the true minutiae thereon. When it is recognized that the Federal Bureau of Investigation alone receives about 30,000 requests a day which involve the determination of the identity of a fingerprint card against an inventory of some 70 million individual's fingerprints, the need for rapid, yet accurate, processing becomes abundantly clear. This requirement for speed and accuracy has not been met by prior systems which process the data in generally a sequential manner. For example, if all other processes await the completion of the longest single process, such as image sensing, the system processing speed is severely limited.

Although prior systems convert the actual fingerprint images as impressions to binary images, they do not provide the gray level information contained in the actual image or impression of the fingerprint. Such information is extremely valuable for identification accuracy in that many of the false minutiae (such as those caused by variations in backgrounds, illumination, source noise and electronic noise) can be efficiently eliminated with a knowledge of the gray level information. One prior system disclosed in U.S. Pat. No. 3,582,889 attempts to eliminate "noise" or "interference" by the provision of a majority decision circuit which performs a three point or bit averaging function at the expense of cutting in half the resolution of the fingerprint images or impressions. This is equivalent to disregarding half the potentially usable data in the fingerprint. Moreover, although some interference is eliminated, interference signals which are greater than the width of one bit are retained. In other words, this prior system makes the assumption that interference is never more than one bit wide.

That the present invention accomplishes the above mentioned objectives and others as well as overcoming the above mentioned disadvantages and others will become apparent as the description thereof proceeds.

The present invention provides a pattern recognition apparatus which is especially adapted for the recognition or identification of fingerprint images or impressions and/or other similar patterns. More particularly, the present invention provides a system for rapidly and accurately identifying the characteristic points of a fingerprint which points are known as minutiae.

According to the present invention, a fingerprint impression or image is scanned by high resolution scanning means such as a flying spot scanner, the signals from which are converted to a digitally encoded image containing sufficient levels of the gray scale information contained in the actual image such that false indications of minutiae can be reduced to a minimum even in seriously degraded regions of the fingerprint image. The encoded image containing the gray scale information is filtered and thresholded by suitable circuits to provide a binary black and white image which has been enhanced or corrected for the many variations noted previously (such as gaps and blots) to thereby eliminate a maximum number of false minutiae prior to subsequent detection processes.

The filtering and thresholding is accomplished by image enhancement means which combines the data in such a manner as to provide an output data sample for each input data sample or fingerprint image spot location which has been scanned. There is thus no loss in resolution or definition in the conversion from gray level information to black and white information. Each output data sample indicates by a 1 or 0 value whether the corresponding fingerprint image spot is a black or white point in the image. This decision for each image spot is based both upon a comparison of the spot density with the average density in the region of the spot and on an estimation of the direction and location of fingerprint image ridges and valleys in the vicinity of the spot. The image enhancement means performs computations using data on all points in the vicinity of the spot for which it is next going to output a black or white data value. These computations are performed in parallel upon all gray level data values corresponding to spots in the fingerprint image.

There is further provided pre-editing means in the form of comparison circuits which responds to data from the image enhancement means and functions to inhibit further processing of spots the local area average gray level of which is not between predetermined limit values. In other words, if the difference between the gray levels of the darkest and lightest linear arrays of points passing through the current point of interest is too little, then further processing of the local area about the current spot is prevented, thereby gaining efficiency and speed while still retaining accuracy.

A minutiae detection system consisting of various circuit means is provided to perform a pattern recognition function upon the flow of data from the output of the above mentioned components. Each sample input to such detection system has a value 1 or 0 indicating a black or white image point, respectively and which corresponds to a spot in the original fingerprint image. Information or data samples corresponding to spots in a local area of the fingerprint image around the instantaneous or current spot of interest is acquired from a memory and analyzed. The current spot can thus be considered to be in the center of a window through which a small segment of the fingerprint image is being "viewed" and is one element of a contiguous area of blacks or whites (ones or zeros) within the window. The data samples comprising the contiguous area within the window are transferred to a new window in which all other samples in the window are zero. That is, all portions of the fingerprint image in the window which are of the same binary value as the area passing through the center of the window but are not contiguous thereto are deleted. If the original area passing through the center of the window consists of points of value 0, then the entire array of data in the window is reversed. This enables bifurcations to be detected as simply negative ridge endings.

The detection system then determines whether the contiguous area within the window intersects more than one segment of the edge thereof and several other geometric properties of the contiguous area, including its area in the window, the extent of the window edge intersected, the regularity of the perimeter, the number of zero data samples (holes) within the contiguous area and the perimeter thereof within the window. These determinations are each compared to acceptable limits both separately and in combination, resulting in a decision as to whether the contiguous area can be classified as a minutia (ridge ending or ridge branch) or as no minutia. If it is classified tentatively as a minutia, the orientation thereof is recorded together with the location thereof.

Means are further provided for comparing the location and orientation of each minutia with those of all minutiae in a nearby area of the fingerprint image. If the orientation and location and type (ridge branch or ridge ending) all fall within predetermined limits, both separately and in combination, then the two minutiae being compared are considered to be duplicate detections of the same minutia. In this case the locations of the detections are averaged and the orientation of the minutia which extends furthest into its window is classified as the true orientation.

Additionally, post-editing means are provided which include means to reject as false apparent minutiae which are oppositely directed. If a pair of minutiae is found to be of the same type having sufficiently close locations and orientations that are within a predetermined tolerance of being in the opposite direction, then the two minutiae are adjudged false ridge endings or branches caused by a ridge gap or a blot in a valley of the fingerprint image and, as such, are deleted.

It is accordingly an object of the present invention to provide an automatic fingerprint or similar reader which provides highly repeatable and accurate encoding of the location of characteristic points in the imagery.

A further object of the present invention is to provide image enhancement means to eliminate imperfections in the imagery and which processes data in parallel such that the image sensing apparatus is not forced to delay its operation until such enhancement means completes its operation. Total image processing time is thus reduced from that which would obtain without parallel digital processing.

A still further object of the present invention is to provide area pre-editing means which does not require significant separate data processing to edit out large areas of the image which should not be further processed, thereby saving substantial processing time.

Another object of the present invention is to provide detection means for characteristic points such as minutiae which examines every point in the image for the occurrence of a minutiae and can detect the same minutiae several times in passing over the entire image. A high degree of redundancy is thus a part of the detection process which greatly reduces the probability of missed minutiae.

It is also an object of the present invention to provide a post-editing subsystem which substantially reduces the probability of detecting false minutiae by detecting and eliminating tentative minutiae detections caused by scars, warts and other defects in both the original fingerprint and the fingerprint image imprinting process.

Another object of the present invention is to provide a minutiae identification system comprising of a sequential series of processes which operate simultaneously to ensure the achieval of high-speed processing.

Other objects and advantages of the present invention will become apparent as the detailed description thereof proceeds.

For a fuller understanding of the present invention reference should now be had to the following detailed description thereof taken in conjunction with the accompanying drawings, wherein.

Figure 1:
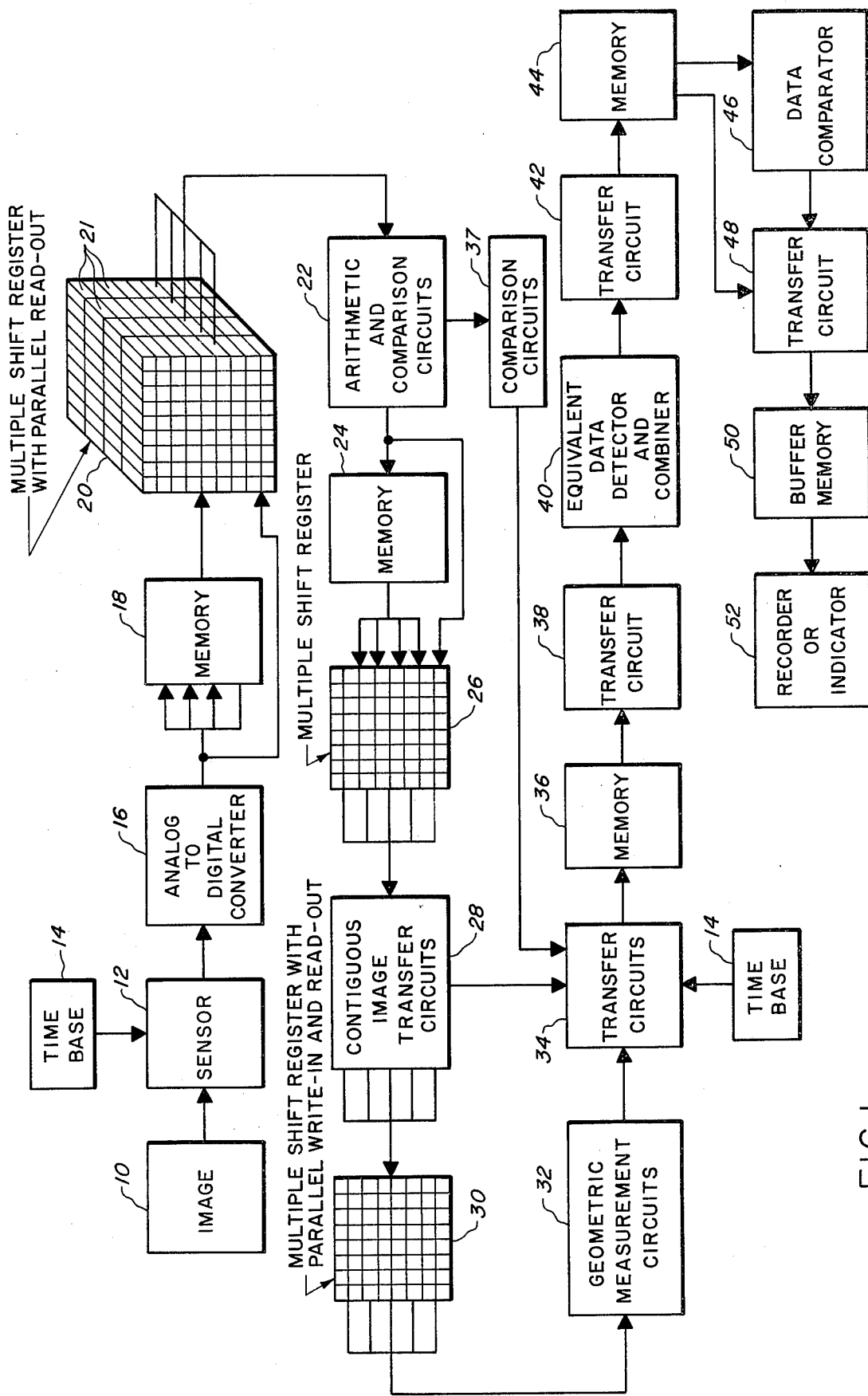
FIG. 1 is a schemtic block diagram of the complete system according to the present invention.

Referring now to FIG. 1, the image 10 which may comprise a fingerprint on a card, an actual finger placed against an optical surface or any other suitable input containing the intelligence to be identified. Suitable sensing means, generally depicted at 12, is provided to develop an output signal which is a function of the input image 10. Such sensing means may conveniently comprise a flying spot scanner which is synchronized, to all other components of the system, by a time base 14 as is conventional. Since the scanner generates signals sequentially from each point of the image all the other components of the system utilize the information therefrom as it is generated. It is not necessary to wait for further processing until the complete image has been scanned nor is it necessary to provide shift register or memory capacity large enough for the total image. For example if the number of points in the image which are resolved by the flying spot scanner are 512 ×

512 or about 262,000, it might be necessary to utilize only about 5000 of these at one time.

As output analog signals are generated by sensor 12 they are converted to digital signals by a suitable analog to digital converter 16. Converter 16 should contain sufficient threshold circuits to permit a large range of gray scale information to be digitized. In the following description it will be assumed, for illustrative purposes only, that 16 levels of gray scale data has been developed.

The output from converter 16 is fed to storage means 18 which may typically comprise any suitable circulating memory such as a magnetic drum, disc or suitably controlled magnetic core memory, as is well known. As will become apparent hereinbelow memory 18 need only have a capacity to store all the points along a number of lines or rows equivalent to the number of rows contained within the "window" of a multiple shift register 20. Register 20 is of the type having parallel read-out, as is well known. To retain the 16 level gray scale information mentioned above memory 18 and register 20 would have a depth of four bits for each data point. This is depicted schematically at 21 for the register.

Figure 2:
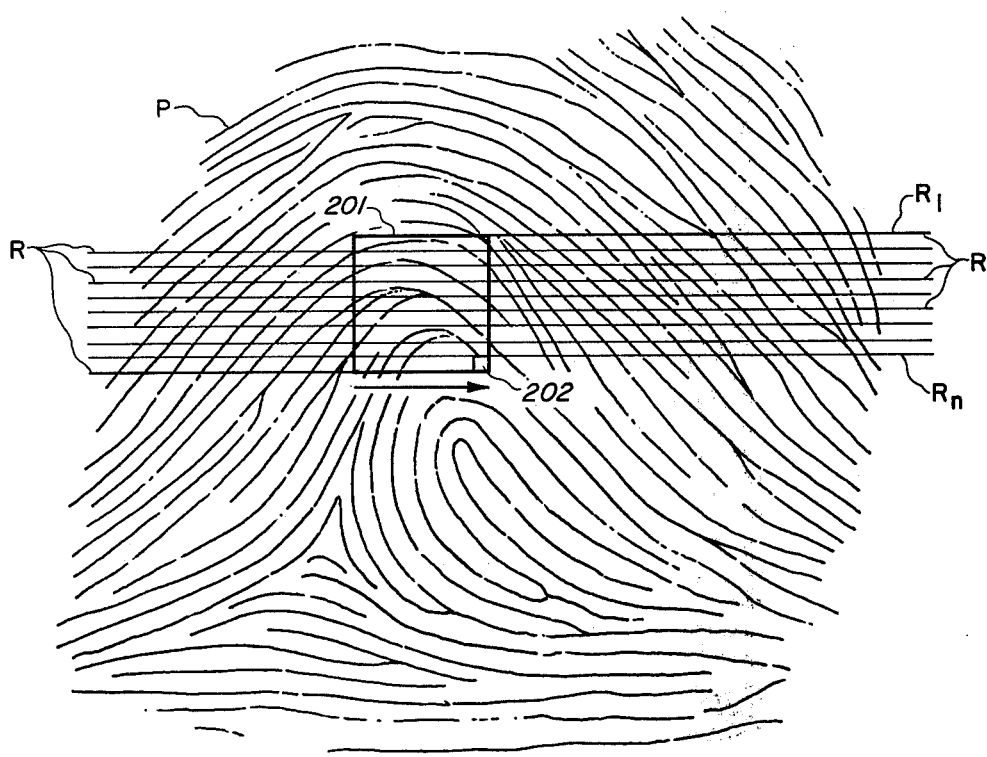
FIG. 2 is a schematic view of the fingerprint image illustrating the manner in which the same is scanned.

As illustrated in FIG. 2 the fingerprint image is depicted schematically at P, superimposed upon which are several sequential scanning lines or rows R (greatly enlarged) of the sensor 12 as it moves in the direction of the arrow. Also superimposed on the image is a rectangular area 201 which represents the "window" or instantaneous area of view of shift register 20. In other words, the shift register 20, at any instant, contains the gray scale value of all image points contained within the area 201, these values all being transferred from memory 18 except for the point 202 which arrives directly from converter 16 as depicted schematically in FIG. 1. The capacity of memory 18 is represented by all the points along each of the rows between $R_1$ and $R_n$ as depicted in FIG. 2, which is significantly less than all of the points contained within the complete fingerprint image. Since the window 202 comprises many rows it is apparent that multiple detections will be made of the same points. As will become apparent hereinbelow, such redundancy enhances the accuracy of the system. Although shift register 20 is depicted as having a nine by nine bit window, other sizes are possible as will be apparent to those skilled in this art.

The gray scale signals emanating from register 20 are delivered to image enhancement means in the form of arithmetic and comparison circuits 22 which function to filter and threshold these signals such that a binary black and white (1 or 0) image is produced which has been corrected for the many variations in contrast and the like which exist between one section of the image and its background and another section of the image and its background. The circuits 22 calculate the average value of the gray-level data for several sets of points in shift register 20 and determines which of such average values differ by the greatest amount from the average of all of these sets. The sets of points so averaged are arranged in radial spokelike fashion through the center of the image area of the shift register 20. Based on these values the center point of the instantaneous image in register 20 is transferred either as black or white (1 or 0) to a memory 24. Thus a white gap in a black ridge will be correctly transferred as black. The circuits 22 may comprise any well known digital and analog summing circuits (such as adders and summing amplifiers), digital and analog comparison circuits (comparators) and analog or digital scaling circuits as is known to those skilled in the art.

Memory 24 fills shift register 26 in parallel fashion to the extent of its capacity which may be illustratively 8 by 8 bits; the last bit coming directly from circuits 22 in the manner previously described with respect to the filling of register 20. Shift register 26 thus contains in its 8 by 8 window an instantaneous binary image of the actual image points embraced thereby.

Contiguous image transfer circuit 28 function to transfer a portion of the binary image in register 26 to multiple shift register 30 having a parallel write-in and read-out ability. The portion of this image transferred or regenerated is that black portion of the image in register 26 which is contiguous to those of the center four points that are black. If the majority of the center four points are black then a potential ridge ending is sought. If the majority of the center four points are white then a valley of bifurcation is sought but since a valley is a negative ridge the image values are reversed or complemented and noted. If half the center points are white and half black then the opposite type of minutiae is sought from that which was sought in the previous window position.

Transfer circuit 28 first transfers the four center points of the image in register 26 directly to the corresponding locations in the register 30. Next, a set of logic circuits are activated, all simultaneously, each of which takes an input signal from one of the points in register 26, other than the four center points, thus the number of such circuits corresponds to the number of points in the shift register 26 less the four center points which for an 8 by 8 bit register would be 60 circuits. Each such logic circuit takes an input from a different point in register 26 and also takes as inputs the eight (or less in case of an edge) points from register 30 which are diagonally, horizontally or vertically contiguous or touching the point therein corresponding to the input to the same circuit from register 26. Each such circuit continuously sets the value of the point in register 30 corresponding to the input point from register 26 to a one (black) if such input point is a one and any of the circuit's inputs from register 30 (the diagonal, horizontal or vertical neighbors) is a one. The simultaneous and continuous actuation of these circuits will cause the black image contiguous to the center to be regenerated by propagation out from the center to the boundaries of such image and the edge of the window if intersected by such image. The circuits will not permit the regeneration or transfer to register 30 of other areas of black in the window in register 26 which are separated by an intervening white area. These circuits consist of well known logic elements such as "and" gates and "or" gates.

Figure 3:
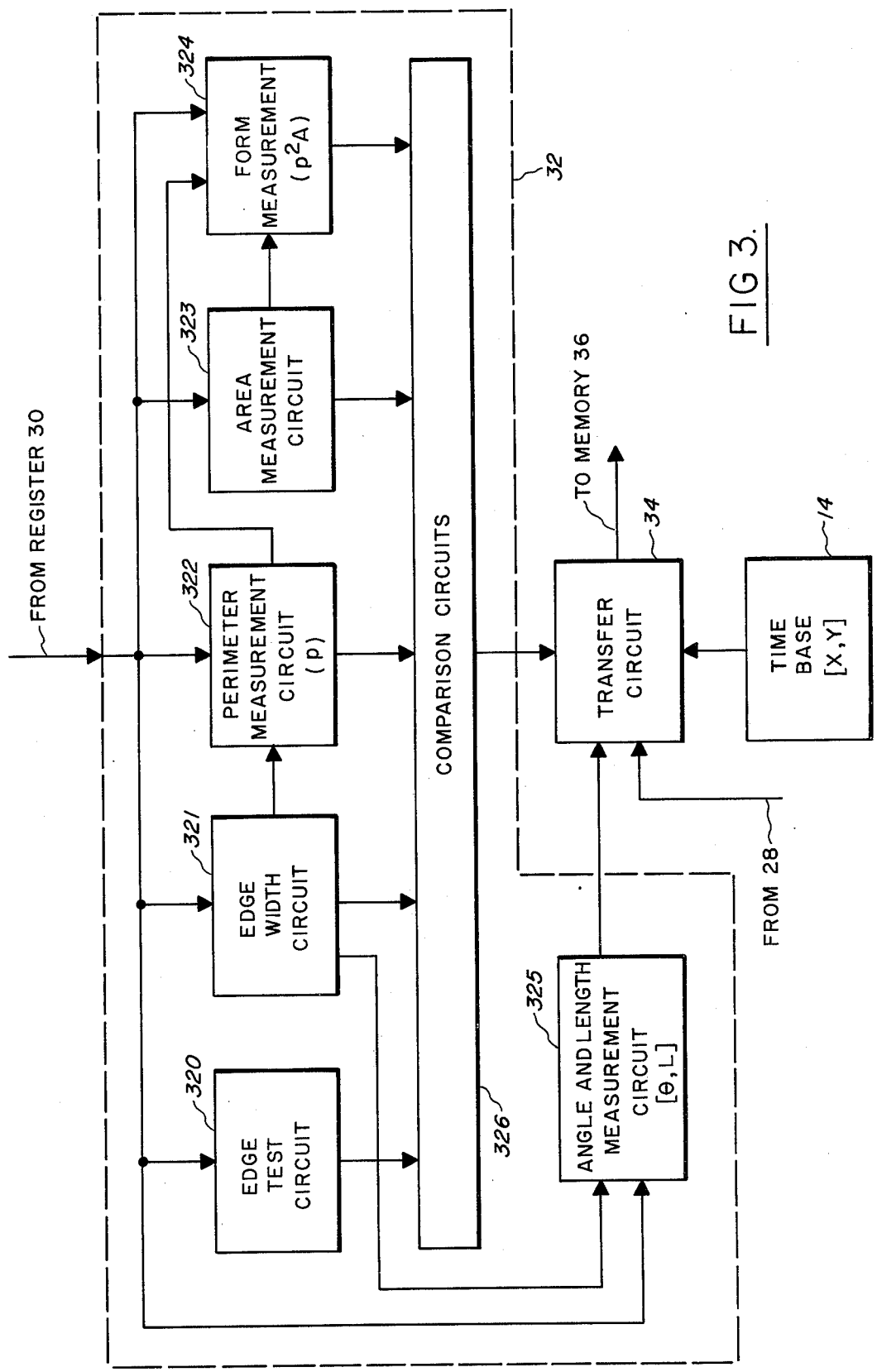
FIG. 3 is a detailed schematic block diagram of one of the components illustrated in FIG. 1.

The image data in register 30 are operated upon by multiple independent measurement circuits contained within element 32 in FIG. 1 and depicted more specifically in FIG. 3 at 320, 321, 322, 323, 324 and 325.

Edge test circuits 320 detects which of eight sets of over lapping points, each spanning one quarter of the edge of the window of shift register 30, have any black points. Circuit 320 further determines whether any two such sets having black points include opposite sides or corners of the window, such occurrence indicating a ridge passing through the window rather than the sought after ridge ending. The structure of edge test circuit 320 may consist of conventional digital logic components such as "or" gates and logical inverters.

Edge width circuit 321 detects the two most widely separated black points on the edge of the image stored in register 30 and counts the number of points along the image edge separating these black points, these together with the two end points is taken to be the edge width of the black image. Conventional digital elements such as counters accomplish this function.

Circuit 322 counts the number of points on the edge of the black area stored in register 30 but not including those points which lie on the edge or boundary of the window of register 30. This number is taken as the internal perimeter of the black area stored in register 30. Conventional digital logic elements such as counters, "or" gates, "and" gates and inverters accomplish this function.

Area measurement circuit 323 counts the number of black points stored in register 30, which is taken to be the area of the black image therein. Conventional digital counters can perform this function.

Form measurement circuit 324 calculates the ratio of the squared value of the perimeter (p) measurement of circuit 322 to the value of the area signal from circuit 323. The result of this calculation is taken to approximately indicate the shape or form of the black area of the image in register 30. If this value is too high or too low it indicates that something other than a fingerprint minutiae is sensed, such as a blot for example. Circuit 324 may consist of conventional digital multipliers and dividers.

Angle and length measurement circuit 325 calculates the angle between the center of those edge points counted by circuit 321 and the black point in register 30 furthest removed therefrom. It also calculates the length L between said center of edge points and the furthest removed point in the black area in the window. The angle $\Theta$ is calculated with reference to the horizontal coordinate direction of the image in register 30. Conventional digital counters, adders and multipliers may perform this function.

The signals from circuits 320, 321, 322, 323 and 324 are fed into comparison circuits 326 which compares the values of each to predetermined ranges. If any one of these signals falls outside its predetermined range no output is generated by circuits 326. Whereas if each and every one of these signals falls within its predetermined range, an output signal is generated by circuits 326 which actuates transfer circuit 34 to permit the storage of the minutia location (defined by time base 14), the minutia angle and length (determined by circuit 325) and the minutia type (indicated by a one bit reversal signal from circuit 28). The structure which comprises circuits 326 may consist of conventional digital logic elements such as comparators, "or" gates, "and" gates and data storage registers as would be known to those skilled in the digital computer field.

The data transferred via 34 into memory 36 is thus preliminarily indicated as the characteristic points or minutiae of the presented image. Some of the data from element 32 is not transferred to memory 36. Areas in the image which are too dark or too light or of insufficient contrast would be unreliable in the detection of fingerprint minutiae and are eliminated. To this end, a signal from comparison circuits 37 to transfer circuit 34 at the appropriate time will inhibit transfer of data from 32 to memory 36.

Circuits 37 receive inputs from circuits 22 and function to pre-edit the gray level binary image for areas that are too light, too dark or of insufficient contrast. As discussed previously, circuits 22 determine the sets of image points having the highest and lowest values from average. Circuits 37 compares the lowest value with a predetermined light area threshold and the highest value with a predetermined dark area threshold. Additionally, the high and low values are subtracted and the difference is averaged with the same difference previously determined for earlier points, which average is then compared against a predetermined contrast value threshold. If any one of the above mentioned thresholds is exceeded then a signal is delivered to transfer circuit 34 to inhibit the transfer of data to memory 36 until the portion of the image develop values within all of such thresholds. The structure of circuits 37 can consist of well known analog or digital logic elements such as summing circuits, comparators and scaling circuits.

Figure 4:
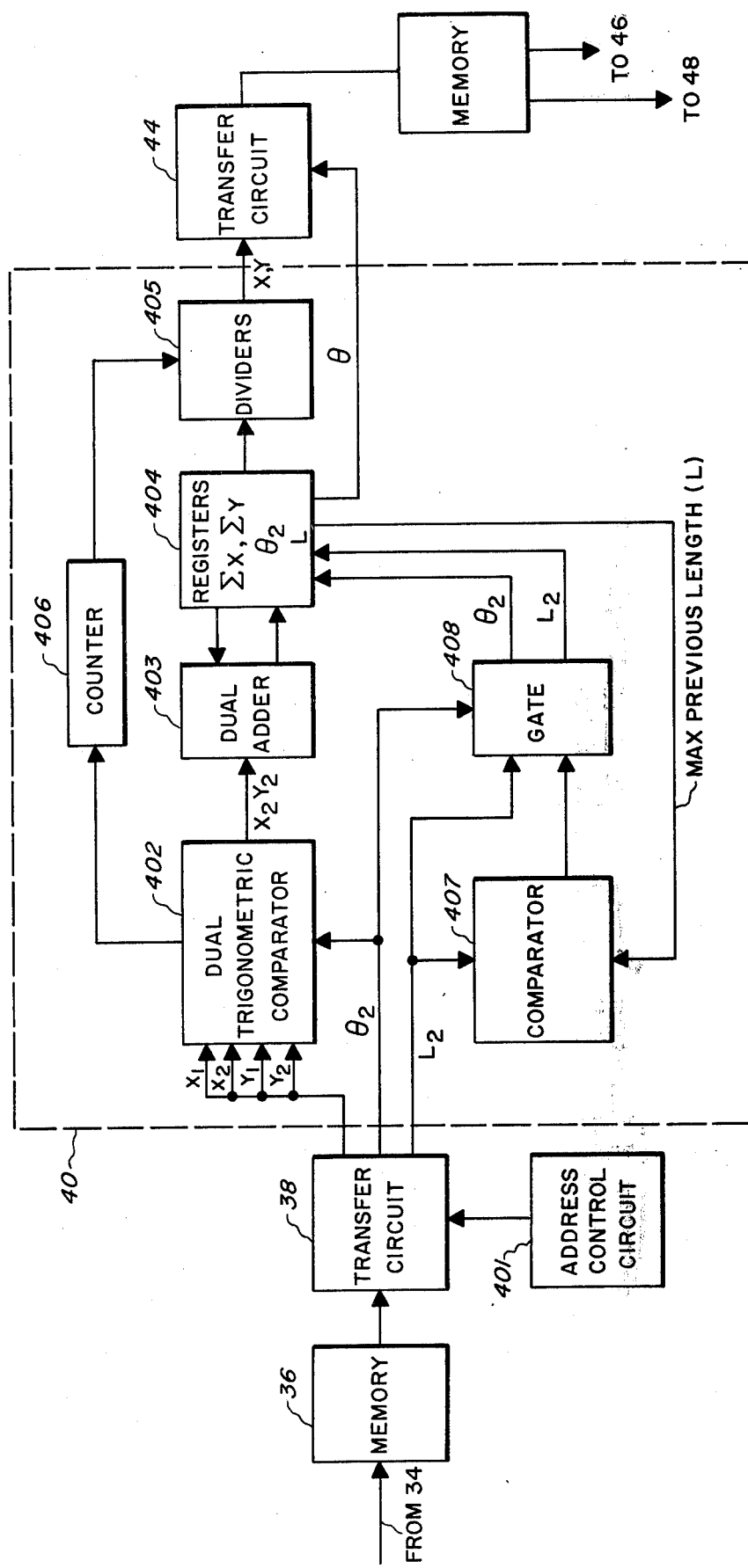
FIG. 4 is a detailed schematic block diagram of the equivalent data detector and combiner of FIG. 1.

The data in memory 36 which is preliminarily identified as minutiae are transferred by transfer circuit 38 to element 40 which functions to merge multiple detections of the same minutia into a single X, Y coordinate at a single value for $\Theta$. In this manner the best minutia coordinate value is retained. Referring to FIG. 4 the equivalent data detector 40 comprises elements which sequentially compares the coordinates of all pairs of points stored in memory 36 under the control of a conventional address control circuit 401 which sequentially addresses elements of the list of minutiae coordinates, angles, lengths and types stored in memory 36 and causes circuit 38 to transfer the same to a dual trigonometric comparator 402. The order in which these minutiae are addressed is such that the coordinates of the first minutiae on the list is compared with the coordinates for all minutiae stored later in the list, then the coordinates of the second minutiae are compared with the coordinates of all the minutiae stored later in the list and so forth until the next to last minutiae is compared with the last minutiae stored. As each minutiae with coordinates $X_1$, $Y_1$ and angle $\Theta_1$ is compared with minutiae later in the list, comparator 402 calculates the difference between $X_1$ $Y_1$ and $\Theta_1$ and the coordinates of each later minutiae $X_2$ $Y_2$ resolved by the angle $\Theta_2$. When the quantities $x_2 - x_1 \cos \Theta_2 + 1$ $y_2 - y_1 \sin \Theta_2$ and $1x_2 - x_1 \sin \Theta_2$ $Y_1 - Y_2 \cos 73_2$ are less than a predetermined limit the coordinates $X_2$ and $Y_2$ are transferred to the dual adder 403 and are added to previously accumulated coordinates therein which were also determined by the comparator to be within these limits of $X_1$ and $Y_1$. The new sum of these coordinates is then stored in register 404. When all later minutiae coordinates have been compared by the comparator 402 to $X_1$ $Y_1$ the accumulated coordinates in register 404 are transferred to the divider circuit 405. The counter 406 counts the number of minutiae whose coordinates have been added together and stored in register 404 during comparisons by comparator 402 with particular minutia coordinates $X_1$ $Y_1$.

The divider 405 divides the accumulated sum of coordinates from register 404 by the minutiae count stored in counter 406. When the comparator 402 detects proximity of minutiae coordinates $X_1$ $Y_1$ and coordinates $X_2Y_2$ and transfers minutiae coordinates $X_2Y_2$ to the adder 403 for addition, the comparator 407 also compares the length of the minutia having coordinates $X_2$ $Y_2$ with the maximum length of all minutiae previously compared to $X_1Y_1$, this maximum length having been retained in one of the registers 404. If the length of the currently transferred minutiae at coordinates $X_2Y_2$ is greater than the previous maximum, then the length value is transferred by means of gate 408 to replace the previous maximum length is one of the registers 404. By this means the stored maximum length is in fact always the maximum length encountered to the current time. When a new value of the maximum length ls is so stored in one of the registers 404, the angle $\Theta_2$ for this minutia is stored in another of the registers 404 replacing any previous angle $\Theta$ stored during comparisons with minutiae coordinates $X_1Y_1$.

When all minutiae with coordinates $X_2Y_2$ have been compared with each particular minutia $X_1Y_1$ and the aforementioned division of coordinates by divider 405 has occurred, the data divided coordinates and the last stored value of the angle $\Theta_2$ are transferred by circuits 42 from divider 405 and a register of 404 to memory 44. In this manner all identical minutiae are detected and merged with a single minutiae which has the maximum length.

Memory 44 has stored therein the coordinates and orientations of all those points in the image which have been identified as characteristic points or minutia (in the case of fingerprint identification). Included among this list of minutia in memory may be some ridges that have breaks or discontinuities that have been erroneously identified as ridge endings. To this end, a comparator 46 compares the data in memory 44 and will not permit actuation of transfer circuit 48 for those minutia whose X and Y coordinates are within a predetermined range of each other and whose angles $\Theta$ differ by 180 degrees plus or minus a predetermined angular tolerance. The comparator 46 may typically comprise conventional digital or analog adders, subtractors and comparators. All other data in memory 44 is transferred to a buffer memory 50 from which the identified minutia may be read-out and/or recorded by recorder or indicator 52, as is conventional.

Although a preferred embodiment of the present invention has been described in sufficient detail to enable one skilled in the art to practice the same changes will obviously occur. It is therefore intended that the invention be limited only by the scope of the appended claims.

I claim:
1. Pattern recognition apparatus enabling the determination of the coordinates and angular positions of characteristic points such as fingerprint minutiae, comprising;
   a. sensing means developing a plurality of signals in response to a presented pattern containing characteristic points which are to be identified,
   b. conversion means responsive to said signals for converting said pattern into a binary encoded image containing many levels of gray scale data,
   c. temporary storage means for temporarily storing in a predetermined sequence portions of said data, which portions comprise sets of points corresponding to said binary encoded image, each point of which having a value indicative of the gray scale level thereof,
   d. means for comparing and averaging said data in said storage means for converting said data into a second binary encoded image comprised of sets of points, each containing one of two levels of gray scale data and which image has been corrected for imperfections in said presented pattern, said means comprise a plurality of logic circuits all of which simultaneously compare and average portions of said data,
   e. continuity means for detecting only those points of said second binary encoded image that are contiguous to a predetermined set of coordinates in said presented pattern, said means comprise a plurality of continuity logic circuits all of which simultaneously detect contiguous points located in portions of said second binary encoded image whereby the detection of all points therein is simultaneous,
   f. means for detecting and determining values indicative of various geometric properties of said contiguous points including the coordinates and angular positions thereof and comparing the same with a plurality of predetermined threshold values, and
   g. characteristic point storage means for receiving the coordinate and angular positions of said contiguous points which fall within said threshold values.

2. The apparatus according to claim 3, further comprising:
   h. means responsive to said characteristic point storage means for determining which of said contiguous points have substantially the same coordinates and angular positions.

3. The apparatus according to claim 3, wherein each of said comparing and averaging logic circuits comprise;
   means for comparing the average value of a set of points of said first mentioned binary encoded image, said set containing as one of its points a central point in said temporary storage means, with the average of all of said sets of points in said temporary storage means whereby said central point is converted to a point in said second binary encoded image as a function of said average of said set and the average of all of said sets.

4. The apparatus according to claim 5, wherein said sets of points in said temporary storage means to which all of said logic circuits are responsive are arranged in radial spoke-like fashion through said central point.

5. The apparatus according to claim 3, wherein each of said continuity logic circuits detect the value of four central points in said second binary encoded image and detect the value of an additional point therein and is responsive to the output of others of said continuity logic circuits each of which detects as one of its four central points a point contiguous to said additional point for detecting the value of said contiguous point.

6. The apparatus according to claim 3, wherein each of said continuity logic circuits detect the value of four central points in said second binary encoded image and detect the value of an additional point therein and is responsive to the output of others of said continuity logic circuits each of which detects as one of its four central points a point contiguous to said additional point for detecting the value of said contiguous point.

7. The apparatus according to claim 1, wherein each of said continuity logic circuits detect the value of four central points in said second binary encoded image and detect the value of an additional point therein and is responsive to the output of others of said continuity logic circuits each of which detects as one of its four central points a point contiguous to said additional point for detecting the value of said contiguous point.

* * * * *